(12) United States Patent
Ferguson et al.

(10) Patent No.: US 6,280,420 B1
(45) Date of Patent: Aug. 28, 2001

(54) REACCESSIBLE MEDICAL NEEDLE SAFETY DEVICES AND METHODS

(75) Inventors: F. Mark Ferguson, Salt Lake City; Mark Nelson, Sandy; David L. Thorne, Kaysville; Gale Thorne, Jr., Bountiful, all of UT (US)

(73) Assignee: Specialized Health Products, Bountiful, UT (US)

( * ) Notice: Subject to any disclaimer, the term of this patent is extended or adjusted under 35 U.S.C. 154(b) by 0 days.

(21) Appl. No.: 09/433,449

(22) Filed: Nov. 4, 1999

(51) Int. Cl.[7] ................................................. A61M 5/32
(52) U.S. Cl. .......................... 604/198; 604/263; 604/192
(58) Field of Search ................................... 604/263, 264, 604/268, 272, 187, 192, 198, 110

(56) References Cited

U.S. PATENT DOCUMENTS

| | | | |
|---|---|---|---|
| Re. 34,045 | 8/1992 | McFarland | 604/198 |
| 3,587,575 | 6/1971 | Lichtenstein | 128/215 |
| 4,040,419 | 8/1977 | Goldman | 128/215 |
| 4,106,621 | 8/1978 | Sorenson | 206/365 |
| 4,270,536 | 6/1981 | Lemelson | 128/218 |
| 4,772,272 | 9/1988 | McFarland | 604/198 |
| 4,790,828 | 12/1988 | Dombrowski | 604/198 |
| 4,795,432 | 1/1989 | Karczmer | 604/110 |
| 4,840,619 | 6/1989 | Hughes | 604/187 |
| 4,846,811 | 7/1989 | Vanderhoof | 604/263 |
| 4,874,382 | 10/1989 | Lindemann | 604/195 |
| 4,874,384 | 10/1989 | Nunez | 604/198 |
| 4,911,694 | 3/1990 | Dolan | 604/198 |
| 4,911,706 * | 3/1990 | Levitt . | |
| 4,929,241 | 5/1990 | Knlli | 604/263 |
| 4,935,012 | 6/1990 | Magre | 604/192 |
| 4,935,013 | 6/1990 | Haber et al. | 604/192 |
| 4,936,830 | 6/1990 | Verlier | 604/110 |
| 4,985,021 | 1/1991 | Straw | 604/198 |
| 5,000,744 | 3/1991 | Hoffman | 604/232 |
| 5,057,089 | 10/1991 | Greco | 604/198 |

(List continued on next page.)

FOREIGN PATENT DOCUMENTS

| | | | |
|---|---|---|---|
| 0 654 281 A2 | 5/1995 | (EP) | A61M/5/32 |
| 0 705 613 A2 | 4/1996 | (EP) | A61M/5/31 |
| 0 457 477 B1 | 1/1998 | (EP) | A61M/5/32 |
| 0 815 888 A2 | 1/1998 | (EP) | A61M/5/32 |
| 0 815 890 A2 | 1/1998 | (EP) | A61M/5/32 |
| 0 819 441 A1 | 1/1998 | (EP) | A61M/5/32 |
| 0 553 308 B1 | 2/1998 | (EP) | A61M/5/32 |
| 0 585 391 B1 | 2/1998 | (EP) | A61M/5/32 |
| 0 485 345 B1 | 3/1998 | (EP) | A61M/5/32 |
| 0 832 659 A2 | 4/1998 | (EP) | A61M/5/32 |
| 0 832 660 A2 | 4/1998 | (EP) | A61M/5/32 |
| 0 626 924 B1 | 5/1998 | (EP) | B65D/83/10 |
| 0 603 365 B1 | 9/1998 | (EP) | A61M/5/32 |
| 0 597 857 B1 | 10/1998 | (EP) | A61M/5/32 |
| 10076007A | 3/1998 | (JP) | A61M/6/32 |
| 10127765A | 5/1998 | (JP) | A61M/5/178 |
| WO 98/07463 | 2/1998 | (WO) | A61M/5/32 |
| WO 98/10816 | 3/1998 | (WO) | A61M/5/32 |
| WO 98/11928 | 3/1998 | (WO) | A61M/5/32 |
| WO 98/13081 | 4/1998 | (WO) | A61M/5/00 |

*Primary Examiner*—Sharon Kennedy
*Assistant Examiner*—Catherine Serke
(74) *Attorney, Agent, or Firm*—Paul S. Evans; Gale H Thorne

(57) ABSTRACT

A retractable and extendable medical needle protective shield which provides opportunity for accessing and reaccessing a medical needle and associated sharpened needle tip and recovering the needle and tip for safety between accesses. The shield includes a needle guide which assures the needle tip is untouched by any part of the shield as the shield is displaced to cover and uncover the needle. A releasable latch is provided to guard against inadvertent removal of the protective shield between accesses. An unreleasible latch is also provided to secure the shield relative to the latch preparatory to final disposal.

11 Claims, 8 Drawing Sheets

U.S. PATENT DOCUMENTS

| | | | |
|---|---|---|---|
| 5,139,489 | 8/1992 | Hollister | 604/192 |
| 5,147,303 | 9/1992 | Martin | 604/110 |
| 5,154,285 | 10/1992 | Hollister | 206/365 |
| 5,176,656 | 1/1993 | Bayless | 604/198 |
| 5,195,983 | 3/1993 | Boese | 604/192 |
| 5,232,455 | 8/1993 | Hollister | 604/192 |
| 5,246,427 | 9/1993 | Sturman | 604/192 |
| 5,246,428 | 9/1993 | Falknor | 604/198 |
| 5,256,153 | 10/1993 | Hake | 604/198 |
| 5,290,255 | 3/1994 | Vallelunga | 604/197 |
| 5,304,137 | 4/1994 | Fluke | 604/110 |
| 5,348,544 | 9/1994 | Sweeney | 604/192 |
| 5,356,392 | 10/1994 | Firth | 604/198 |
| 5,403,286 | 4/1995 | Lockwood | 604/110 |
| 5,447,501 | 9/1995 | Karlsson | 604/198 |
| 5,466,223 | 11/1995 | Bressler | 604/110 |
| 5,487,733 | 1/1996 | Caizza | 604/110 |
| 5,498,243 | 3/1996 | Vallelunga | 604/197 |
| 5,533,980 | 7/1996 | Sweeney | 604/192 |
| 5,643,220 | 7/1997 | Cosme | 604/192 |
| 5,695,474 | 12/1997 | Daugherty | 604/162 |
| 5,738,665 | 4/1998 | Caizza | 604/263 |
| 5,746,726 | 5/1998 | Sweeney | 604/263 |
| 5,814,018 | 9/1998 | Elson | 604/110 |
| 5,823,997 | 10/1998 | Thorne | 604/110 |
| 5,843,041 | 12/1998 | Hake | 604/198 |
| 5,925,020 | 7/1999 | Nestell | 604/198 |
| 5,957,892 * | 9/1999 | Thorne . | |

* cited by examiner

REACCESSIBLE MEDICAL NEEDLE SAFETY DEVICES AND METHODS

FIELD OF INVENTION

This invention relates generally to safety devices for hollow bore medical needles and particularly to syringe needle devices which employ protective needle shields or sheaths for securely shielding sharp needle tips, both before and after being used in a medical procedure. This invention more particularly relates to removable medical needle shields, sheaths or shrouds which may be used as removable and replaceable protective needle covers. Consistent with such uses, the medical needle may be accessed, covered and reaccessed repeatedly for such purposes as protecting a sharpened needle tip in transit before use, ad interim after a preliminary use, such as filling a syringe with a medication, and being displaced to a safety, needle-covering position after a medical procedure is completed.

PRIOR ART

Problems associated with inadvertent needle sticks are well known in the art of blood sampling, percutaneous medication injection and other medical procedures involving use of medical needles. Ever increasing attention is being paid to needle stick problems due to the contemporary sensitivity of exposure to AIDS, Hepatitis and other serious blood-borne diseases.

Commonly, procedures involving removing a needle from a patient require a technician to use one hand to place pressure at the wound site where the needle is being withdrawn while removing the needle apparatus with the other hand. It is common practice for a tending technician to give higher priority to care for the wound than is given to disposal of a needle. In the case of commonly used, non-safety devices such priority either requires convenience of an available sharps container within ready reach or another means for safe disposal without leaving the patient's side. Providing adequate care, with accompanying safety procedures, is often compounded by patient physical condition and mental state (e.g. in burn units and psychiatric wards). Under such conditions, it is often difficult, if not impossible, to take appropriate action to properly dispose of a used, exposed needle while caring for a patient. Further, common practice of filling syringes with medication in one area and then transporting an uncapped needle (recapping a needle is currently discouraged in U.S. medical practice due to dangers associated with recapping) to a patient area provides a significant opportunity for accidental needle sticks.

Widespread knowledge and history associated with needle care and disposal problems have resulted in conception and disclosure of a large number of devices each of which represents an attempt to provide not only a solution to the problem of needle sticks, but also a device which is commercially viable (i.e. cost and price competitive with currently used non-safety devices). In the case of syringes, current devices which are used to shield syringe needles often require two hands and, in some devices, safety status of needle shields are not readily apparent.

Examples of disclosures of safety devices which protect needles by moving a protective shield over a sharp end of a syringe or other hollow bore medical needle are found in U.S. Pat. Nos. 5,823,997 issued Nov. 17, 1998 to David L. Thorne (Thorne), 5,348,544, issued Sep. 20, 1994 to Sweeney et al. (Sweeney), U.S. Pat. No. 5,246,428 issued Sep. 21, 1993 to Donald W. Falknor (Falknor), U.S. Pat. Nos. 5,256,153 issued Oct. 26, 1993 to Lawrence W. Hake (Hake) and 5,139,489 and 5,154,285, issued Aug. 18, 1992 and Oct. 13, 1992, respectively, to William H. Hollister (Hollister). There are many other examples of safety devices which retract needles into housings, however, this instant invention is more directly related to devices which extend a shield over a needle rather than to those which employ needle retraction.

Thorne discloses a safety needle enclosure which is disposed to rotate about a needle and, upon being displaced to a needle shielding state, forms a substantially rigid part in cooperation with the needle to thereby provide a safety needle shield. The enclosure comprises a plurality of rigid segments serially interconnected by a plurality of intersegment hinges, which are preferably living hinges. The segments are disposed about a medical needle, folded upon each other during the medical procedure and extended, only at the end of the procedure, to form a secure, substantially rigid, single-use safety shroud. During the procedure, the enclosure is folded and conveniently disposed about a proximal portion of the needle. At the end of the procedure, the enclosure is extended to protectively sheath and secure the needle in a substantially rigid structure formed by the combination of the enclosure and the needle.

Sweeney discloses a device comprising a guard which is manually, slidably movable along a needle cannula from a site proximal to a user to a distal site where the needle tip is shielded. The device comprises a hinged arm which extends along the needle cannula and which is moved distally to collapse upon itself to extend the shield over the tip. Access to the tip is denied by a metallic clip. An alternative embodiment is also disclosed by which the manual operation is augmented by a spring. A device based upon Sweeney is currently being distributed by Becton Dickinson and Company, Franklin Lakes, New Jersey in which three separate parts (two injection molded and one metal clip) are used to mechanize the guard. Once the device is extended to shield a needle tip, it should not be reset to recover use of the needle for a subsequent procedure, and is therefore, like the device taught by Thorne, a single-use device. Also, the hinged arm requires activation in the region of the needle itself and comprises parts which are of a size which occasionally impedes a user's line of sight to insertion locations.

Falkner, and related disclosures, disclose devices comprising shields which are automatically releasable to extend distally from a user to cover a needle. The devices comprise latch mechanisms which are manually switched between unlatched and latched positions to free the needle for use and lock the shield over the needle, respectively. Of course, position of the latch mechanism provides a visual interpretation of the safety of the device (i.e. whether or not a latch is engaged), but that is the only safety mechanism and a "missed" indicator of latch mechanism position may be possible in stressful circumstances. When the latch mechanism is in the unlatched position, access to the needle is not only possible, but likely when the front of the device is impacted by a body part. In addition, the shield, though made of transparent material, covers a portion of an attached syringe body until fully extended and may make accurate reading of portions of volume measurement indicia on the syringe body difficult when the syringe is being used in a titrating application.

Hake is representative of disclosure of devices comprising a manually slidable guard which is disposed over a syringe body during a medical procedure involving a medical syringe needle and manually, slidably moved distally into a needle guarding position usually at the end of the procedure.

Commonly users of such devices complain of difficulty of seeing measurement indicia while the guard is disposed over the syringe body and of danger of inadvertent needle sticks while sliding the guard distally to cover the needle. As well, it is generally difficult to determine whether a guard is in a locked or unlocked state when it covers the needle, making an additional possibility of inadvertent needle sticks.

Hollister discloses a needle protection device which may be used with a double-ended needle assembly or with a simpler single needle system. The protection device comprises a substantially rigid housing flexibly connected to a container (for a vacuum tube sampling system) or to a needle hub. To exercise the protection device, the rigid member is pivotally rotated into engagement with an exposed needle of the double-ended needle assembly and is securely affixed to the exposed needle. A major drawback of the needle protection device of Hollister is the size and position of the rigid housing. During use of an assembly or system in a medical procedure, length and position of the housing member is considered by some to be inconvenient. A second drawback is the apparent requirement either for two handed operation to pivot the housing to engage the needle or for the requirement to find and use a stable support surface against which the housing is pressed while the needle is swung into engagement with the housing. In a currently marketed format, an integral container holder version of the device disclosed by Hollister comprises two injection molded parts which permit the housing to be rotated, as much as possible, out of the way during a medical procedure. Such a format requires five injection molded parts, including a disposable needle assembly.

An often occurring circumstance, especially in the use of syringe needles, involves a need to use a needle a plurality of times. As an example, when an intramuscular injection is made, it is common practice to draw contents from a drug vial into a syringe and then inject the contents into a patient. It is desirable to use the same needle for penetrating a membrane on the drug vial and then for injecting the patient. However, the site where contents are drawn from the drug vial may be some distance form a site where the patient is to be injected. Such situations may result in a technician's recapping the needle (a procedure which is currently discouraged and against standard precautions) for transport to the patient. Equally as concerning is another practice of carrying the needle unprotected. Some currently available safety devices, such as those based upon Hake, permit covering and reaccessing a needle; however, other factors, such as those disclosed above have limited acceptance of these safety devices.

Generally, other than acceptance of the type of operation offered by such devices, commercial viability is dependent upon manufacturing cost. Purchase decisions in the area in which these devices are used are very cost sensitive. If gains in either improvement in safety or in labor savings are not found to make a device sufficiently competitive with contemporary items currently on the market, those devices are usually not found to be commercially viable.

BRIEF SUMMARY AND OBJECTS OF THE INVENTION

In brief summary, the novel invention disclosed herein dramatically diminishes known major problems resulting from injury-related needle sticks which occur when needle tips are bared as medical needles are withdrawn from a patient at the end of a needle insertion procedure, but, perhaps more important to general patient welfare, these inventions provide opportunity for fabrication of a very low cost safety needle system which permits access to a medical needle in several steps in medical procedure, while being able to return the needle to the safety of a covering enclosure between the steps.

Basic to the invention is a medical needle device which employs a protective needle shield which may be somewhat similar in form and function to a sheath disclosed in Thorne, but is discernably different in that the shield of the present invention is displaceable to cover and protect a needle tip and which is further displaceable to bare the needle and tip a plurality of times for use throughout a medical procedure. It is further differentially discernable because the needle tip is untouched by the shield in addition to being protectively covered.

For reference, Thorne discloses a foldable needle sheath which is articulated to fold about a medical needle to permit access to the needle in a medical procedure. The sheath is hingeably attached to a structure (e.g. a needle hub or phlebotomy barrel) at a point away from a sharpened needle tip which is later enclosed to protect a user. At the end of the procedure, the sheath is unfolded and extended away from the structure in the direction of the needle tip to encase and thereby protect users from contact with the needle and its tip. To permit the sheath to unfold about the needle, each folded part of the sheath is serially constructed of a plurality of rigid and interconnected segments. At least one segment comprises an orifice through which the needle passes and about which each at least one segment rotates while the sheath is being extended. Each segment is connected to at least one other segment by a hinge, which is preferably a molded, living hinge, and comprises a channel into which the needle is nested when the sheath is fully extended. The sheath comprises a catch which securely affixes the sheath when the needle is captured to be disposed in the sheath. Once the sheath is extended and the needle so captured, the combination of sheath and needle form a substantially rigid member which shrouds the needle and its sharpened tip to provide safety from dangerous contact with the tip and needle. All hingeable attachments are preferably living hinges integrally and concurrently formed with other sheath parts. It is very important to note that, once the sheath of Thorne is extended to protect the needle and its tip, Thorne teaches of no subsequent release of the sheath from being disposed to protect the needle and tip.

In the present invention, a shield is disposed about a needle and tip to provide protection. However, different from the teachings of Thorne, a temporary, releasable latch is provided which may be disengaged to permit the shield to refold and, thereby, permit reaccess to the needle for a subsequent medical procedure. Once each procedure is complete, the shield is again extended and latched to provide a safety cover. Further, a selectively activated unreleasible lock is provided for the protective shield to thereby assure secured needle tip protection at the end of use.

In a preferred embodiment, the shield includes a needle guide, proximally disposed relative to the tip of a needle, which protects the tip from damage through contact with the shield, both, as the protective shield is displaced to cover and shield the needle and as the shield is removed to bare the needle for use. The needle guide is disposed and constrained to travel in alignment with the long axis of the needle and also constrained to facilitate movement of the shield about the needle without contact with the needle tip.

Generally, the device may be configured into at least two temporary or releasable but stable states. In one stable state the shield is constrained to be disposed "out-of-the-way" when the needle is bared for use. In a second releasible stable state, the shield is constrained to be protectively disposed about the needle and needle tip. Further, the device and shield, in combination, include the permanent lock which is securely and unreleasibly affixed to prevent further use of the device when use is complete. Preferably, latches are used to constrain the shield in each of the stable states.

Other important factors in safety needle devices involve whether the device can be effectively used by a single hand and the number of times a needle may be accessed while being maintained in a needle-safe condition between uses. Especially in the case of hypodermic syringe needle devices, ability to access a medical needle from a safety state a plurality of time is very important as it is common practice to prefill a syringe using a needle to access a medical fluid containing vial and then deliver the contents of the syringe to a patient using the same needle.

Generally, the invention provides for single handed operation and for access to a medical needle a plurality of times while protecting a user from inadvertent injury from the needle while protecting the needle and especially its fragile tip from damage when the device is moved to, displaced from or simply disposed within the safety of the shield.

Accordingly, it is a primary object to provide a device having a safety shield for a medical needle and an associated sharpened tip which permits, within desirable and acceptable bounds of safety and efficacy, a plurality of cycles of shielding and baring the medical needle whereby the needle may be covered or otherwise shielded for transport or other non-needle use functions and then safely bared for use more than one time.

It is an important object to provide a medical needle shield which is securely but releasibly affixed to cover and protect the medical needle and its associated sharpened tip in a first state.

It is another important object to provide a medical needle shield which is securely and unreleasibly affixed to cover and protect the medical needle and sharpened tip in a second state.

It is yet another important object to provide a needle guide which is disposed to operate within the shield to assure the sharp tip of the needle is untouched throughout each needle covering and baring procedure.

It is a particularly important object to provide a shield which is folded out-of-the-way in one state whereby a medical needle may be used in a medical procedure and which is unfolded to combine with the medical needle to form a substantially rigid needle shrouding structure which protects against inadvertent contact with a sharpened tip of the needle.

It is a very important object to provide a releasible and lockable needle shield which is both releasible from a needle protective state whereat the needle tip is protectively covered and thereafter displaced to a locked state in which the shield is securely affixed in an extended state to unreleasibly protect the needle tip.

It is also a very important object to provide a needle shielding device which is facilely operable by a single hand.

These and other objects and features of the present invention will be apparent from the detailed description taken with reference to accompanying drawings.

DETAILED DESCRIPTION OF THE ILLUSTRATED EMBODIMENTS

In this description, the term proximal is generally used to indicate relative nearness of a referenced item to a user of a device or a viewer of a perspective drawing of a figure. The term distal is similarly used to indicate relative remoteness. Reference is now made to the embodiments illustrated in FIGS. 1–8 wherein like numerals are used to designate like parts throughout.

Figure 1:
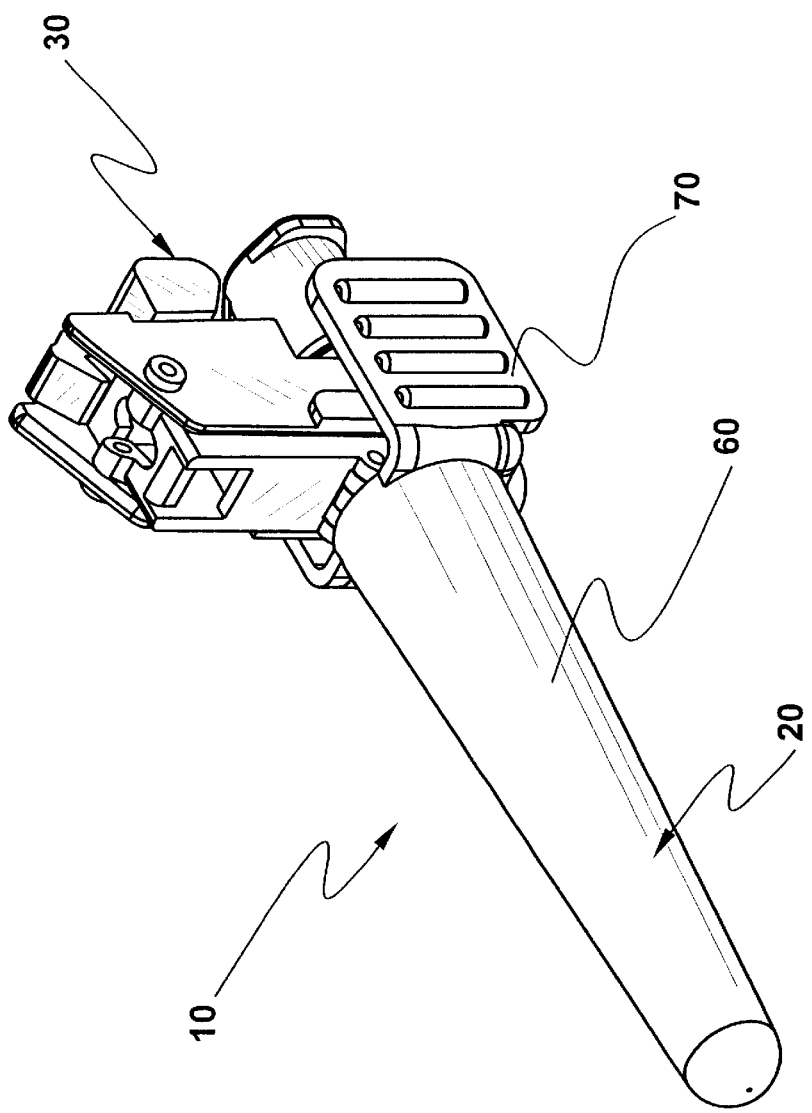
FIG. 1 is a perspective of a medical needle shield assembly with a needle cover and a releasible needle shield.

Reference is now made to FIGS. 1–6 wherein a basic embodiment of the instant invention is disclosed. As seen in FIG. 1, this embodiment is a needle shielding safety device 10. Device 10 is seen to have a needle cover 20 and a needle-hub-shield assembly 30.

Figure 2:
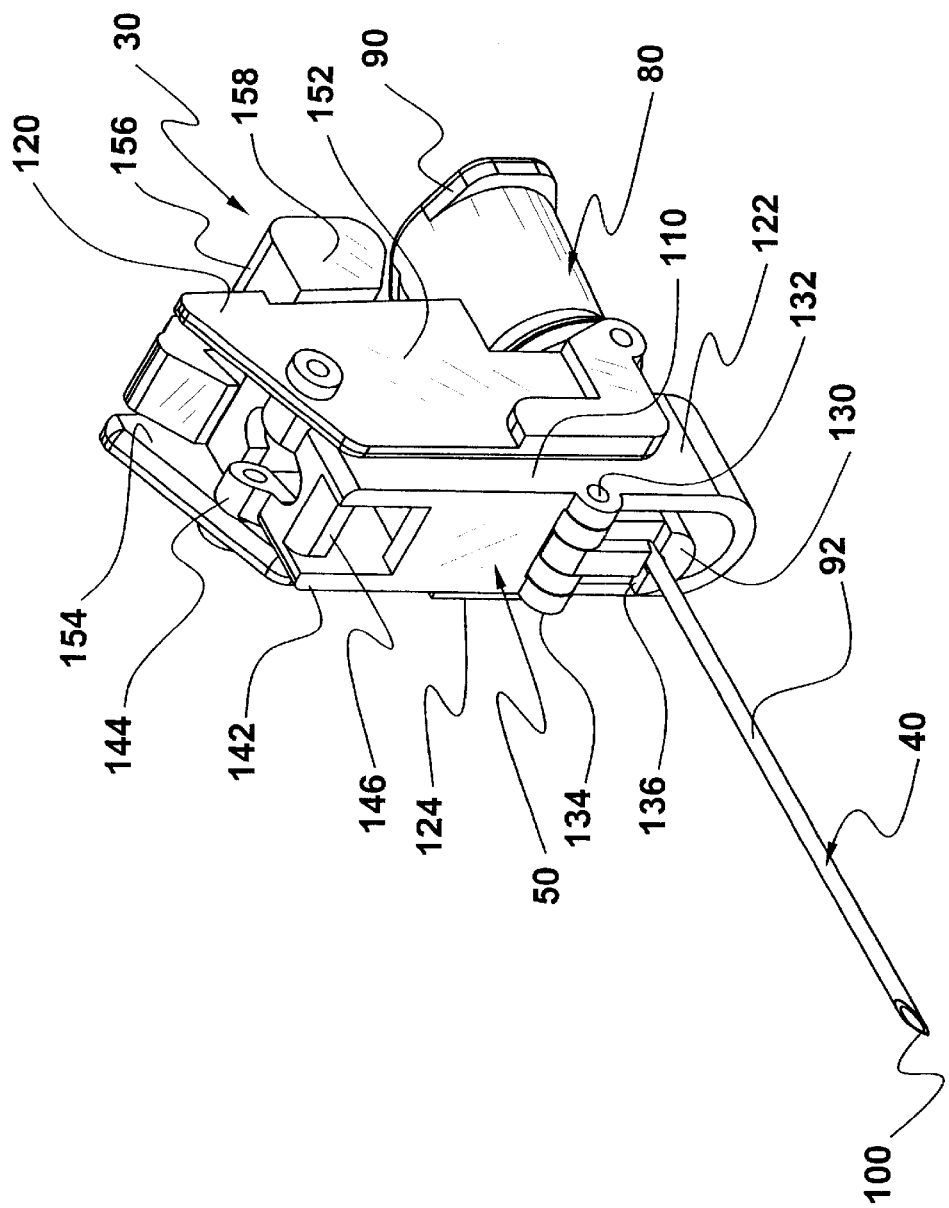
FIG. 2 is a perspective of the medical needle shield assembly of FIG. 1 with the needle cover removed.
Figure 3:
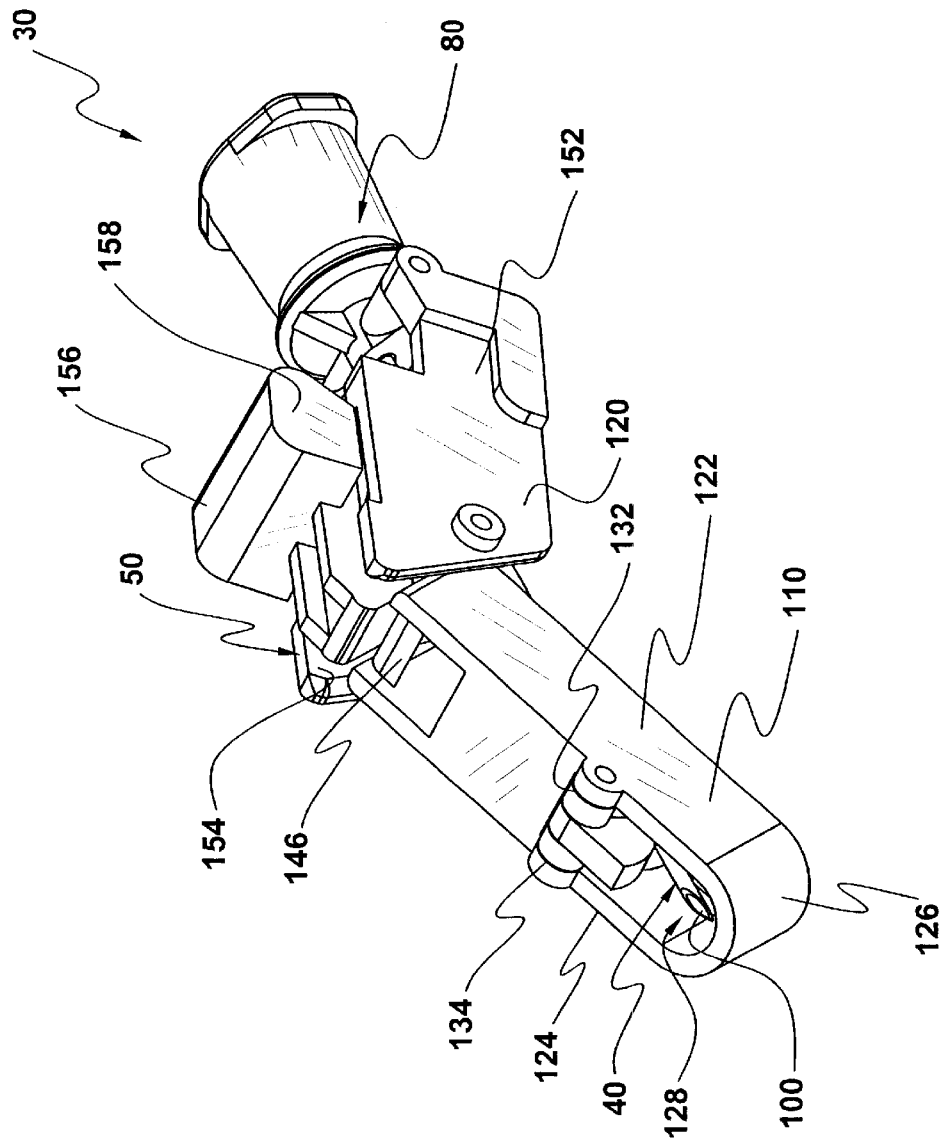
FIG. 3 is a perspective of the medical needle shield assembly of FIG. 2 with the shield partially displaced.

Assembly 30 is better seen in FIG. 2 wherein cover 20 is shown to be removed to expose a medical needle 40 and otherwise concealed distal portions of a foldable needle shield 50. As is apparent from differences between FIGS. 1 and FIG. 2, needle cover 20 has an elongated hollow frustoconical distal part 60, which is similar in form and function to needle covers commonly used for protecting needles prior to use. Cover 20 also has a laterally and proximally disposed guard 70. Guard 70 acts as a keeper against inadvertent shield 50 unfolding or safety actuation, before removal of cover 20 for use of needle 40. Similar to commonly currently available needle covers, needle cover 20 may be formed (e.g. injection molded) from polypropylene or other synthetic resinous material.

It is important to note that for devices which permit reaccessing a medical needle, a cover such as cover 20 may not be necessary. When a shield is securely, but releasibly latched, a device, for example, such as assembly 30, may be deployed in a safe state with a needle 40 being protectively covered by a shield, such as shield 50, as disposed in FIG. 5. The device, so deployed, my then be packaged and shipped is in an antiseptic protective wrap, such as a "bubble pack" without a cover, such as cover 20. Such deployment and elimination of a cover reduces both the cost of the basic device and the cost of discarding ancillary parts.

In addition to needle 40 and shield 50, assembly 30 has a needle hub 80 to which needle 40 is securely affixed and to which shield 50 is hingedly affixed. In this embodiment, hub 80 is seen to comprise a female luer fitting 90, though other flow through hub fitting and connections may be used within the scope of the instant invention. Needle 40 is generally formed from a hollow bore cannula to have an elongated shank 92 and a sharpened tip 100.

Primary to the inventive novelty of this embodiment is shield 50. As may be better seen in FIGS. 3 and 4, shield 50 is formed from two segments, a distal segment 110 and a proximal segment 120. It should be noted that more than two segments may be used to form a foldable needle shield, as disclosed in Thorne.

Figure 6:
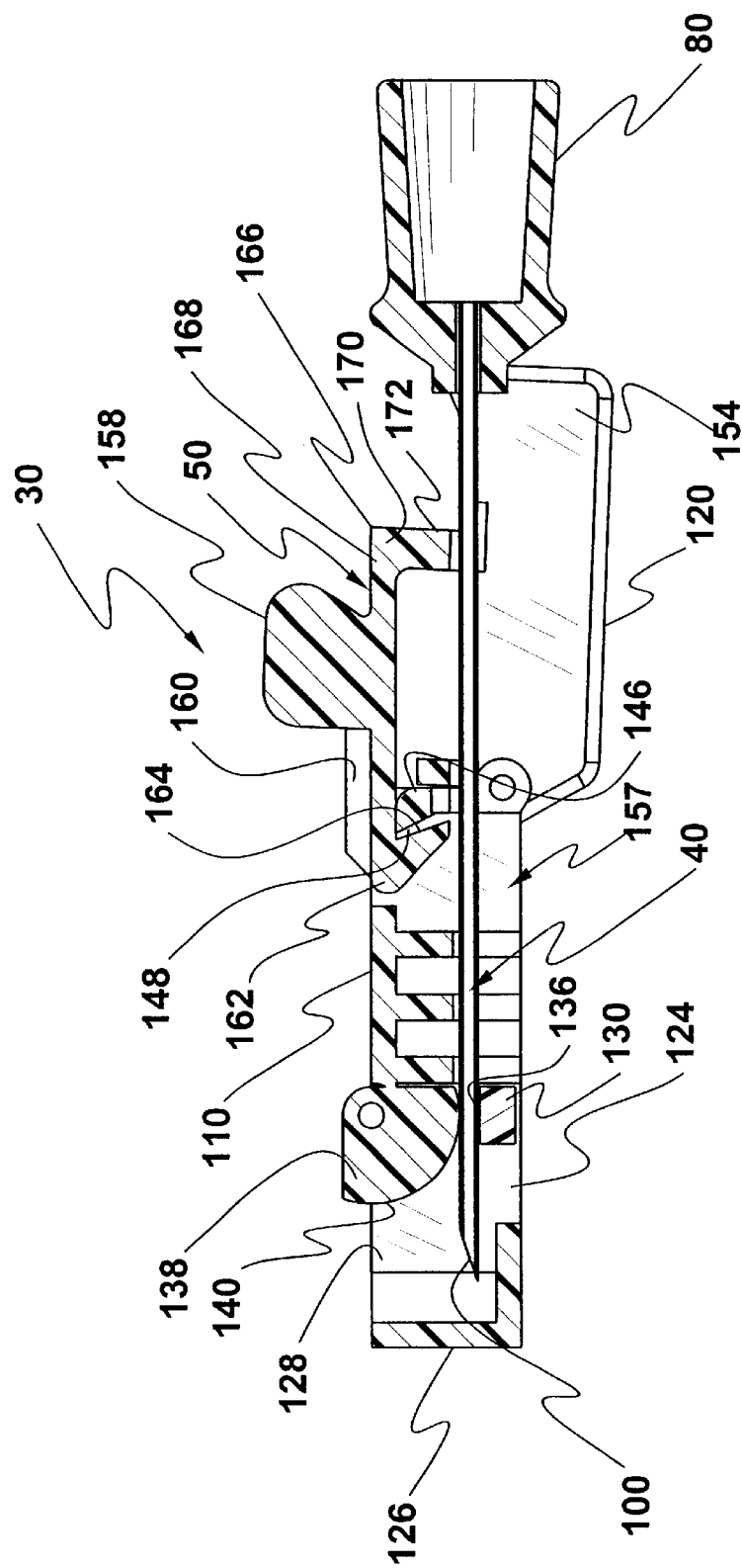
FIG. 6 is a lateral cross section of the medical needle shield assembly as displaced in FIG. 5.
Figure 7:
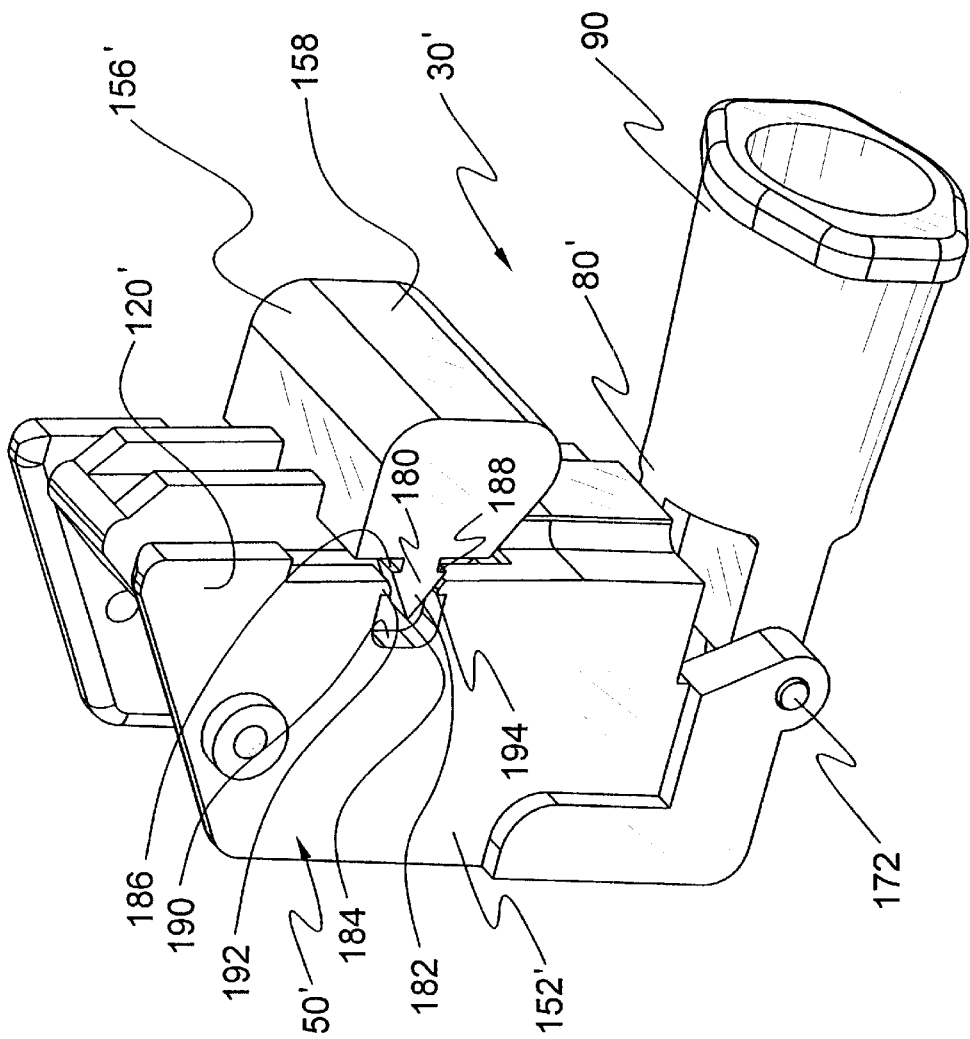
FIG. 7 is a perspective of a medical needle shield assembly which is substantially the same as the assembly of FIG. 2 except that this assembly is seen without a needle and with an unreleasible catch and latch.

Distal segment 110 is made to have a pair of juxtaposed elongated side pieces 122 and 124 and a closed end 126 which is formed to be contiguous with side pieces 122 and 124 and thereby form a hollow needle tip 100 guard recess 128. Note that, as shield 50 unfolds to protect needle 40 and, especially, needle tip 100, tip 100 should make no contact with any parts of distal segment 110. Such contact could jeopardize the structural integrity of a commonly insubstantial and vulnerable tip 100, and therefore, similarly jeopardize continuing use of needle 40. To assure that needle tip 100 is guided in and out of distal segment 110 in both cases where shield 50 is unfolded to become a shroud and refolded to bare needle tip 100 for further use, a yoke 130 is affixed to side members 122 and 124 by a pair of hinges 132 and 134, respectively (see FIG. 2). Yoke 130 has a needle bearing surface 136 upon which needle 40 glides as distal segment 110 rotates about needle 40 during folding and unfolding. Further, as best seen in FIG. 6, distal segment 110 has an arcuately formed guide 138 disposed to provide a convex guide surface 140 between needle 40 and needle bearing surface 136. In combination, yoke 130 and guide 138 act to deflect or lift needle 40 from guard recess 128 as shield 50 is folded and to guide needle 40 into guard recess 128 as shield is unfolded thereby protecting tip 100 from contact with shield 50. For these reasons, such combinations may be referenced as guides or bearings herein.

In addition, segment 110 has a pair of proximally disposed connective hinges 142 and 144 (see FIG. 2) by which segment 110 is hingedly affixed to segment 120. It should be noted that all or part of the hinges of assembly 30 may be formed as living hinges by injection molding all or any combination of parts of hub 80, proximal section 120 and distal section 110, if an appropriate material such as polypropylene is used, as disclosed in Thorne. Also proximally disposed is a medially aligned transverse bar 146 which has a sloped face 148 (see FIGS. 4 and 6). Sloped face 148 is so sloped to act as a catch for a latch disposed in proximal segment 120 and described in detail hereafter.

Referring now to FIGS. 2–5, proximal segment 120 is seen to comprise a pair of lateral sides 152 and 154 joined by a top piece 156. Note, as may be seen in FIGS. 5 and 6, that sides 122, 124, 152 and 154 cooperate to form a channel 157 which acts as a protective side guard for needle 40 and tip 100 when shield 50 is extended. Top piece 156 has a prominent button 158 superiorly disposed for easy digital access. Integral to button 158 is a distally extending arm 160 which terminates in an inwardly directed latch hook 162 (see FIG. 6). Latch hook 162 has a proximally disposed latch face 164 (seen in FIG. 4) which is disposed to interactively latch against a catch formed by sloped face 148 when shield 50 is completely unfolded.

Figure 4:
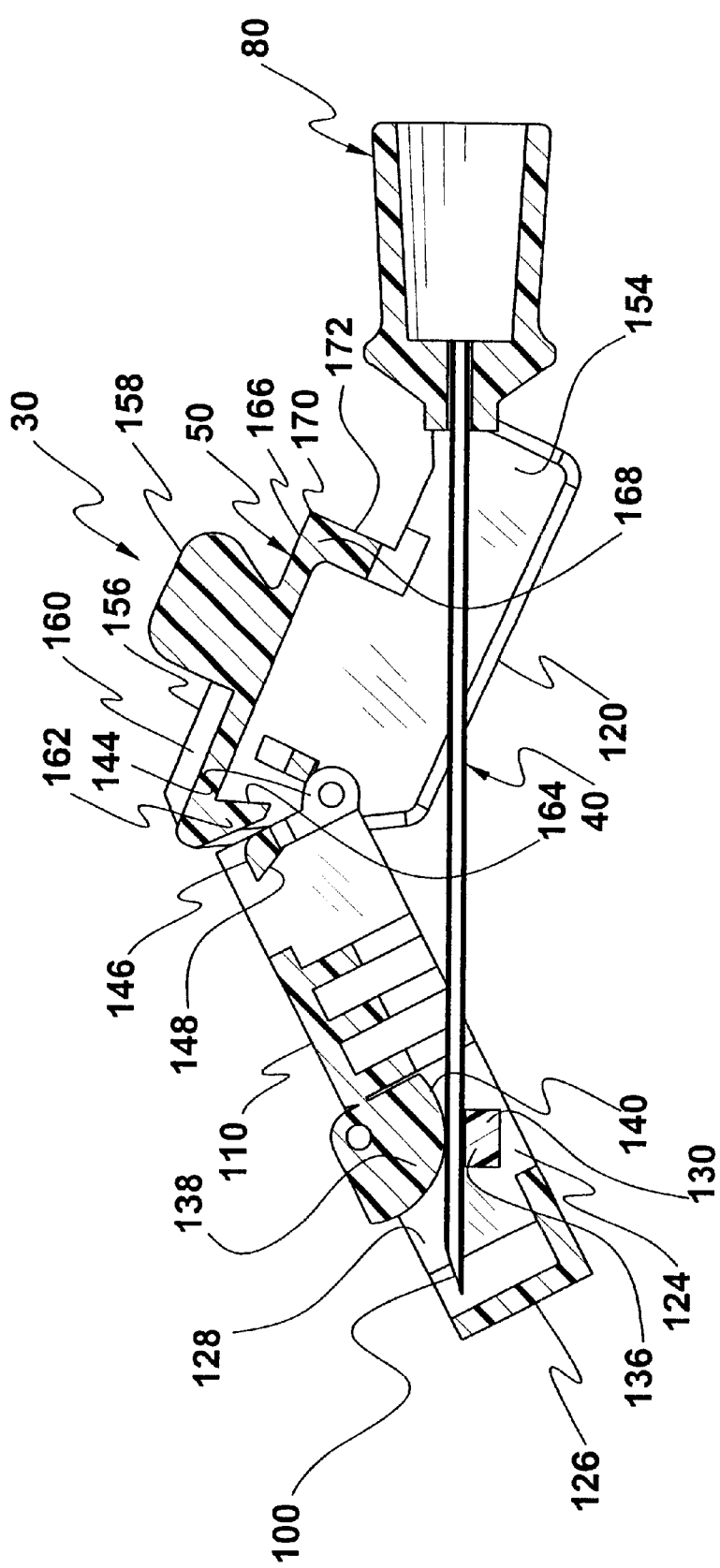
FIG. 4 is a lateral cross section of the medical needle shield assembly as seen in FIG. 3.

Also integral with button 158 is a proximally extending arm 166 (see FIGS. 4 and 6). Arm 166 is bent at an elbow 168 to terminate in an inwardly extending cross member 170. Cross member 170 is transversely, securely affixed to lateral sides 152 and 154 (see FIG. 3) in a cantilevered fashion such that retractive force applied to button 158 causes arm 160 to rotate upwardly and outwardly relieving the catch formed at faces 148 and 164 thereby permitting shield 50 to be folded and thereby lift needle 40 from confinement of shield 50 for use in a medical procedure.

Figure 5:
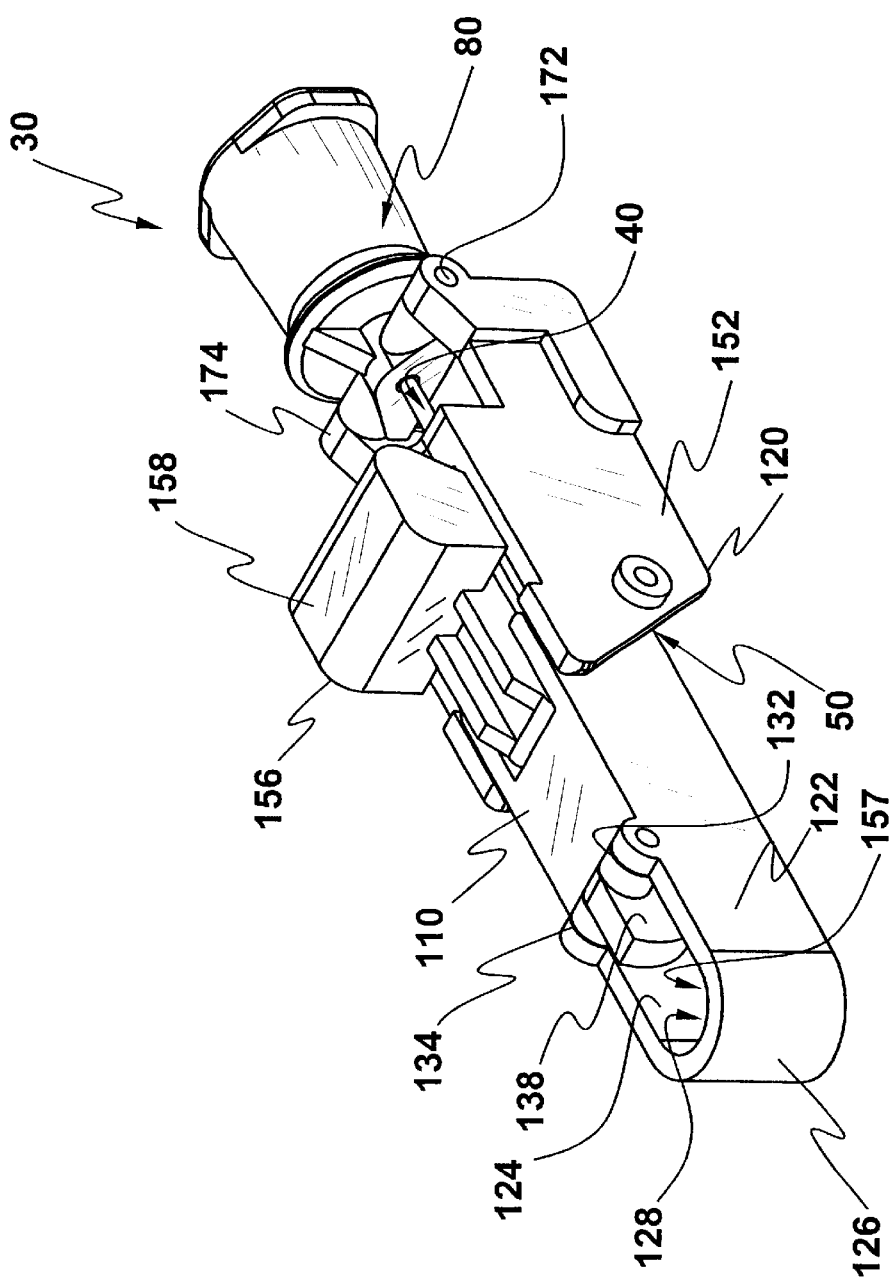
FIG. 5 is a perspective of the medical needle shield assembly of FIG. 3 with the shield fully displaced to protectively cover the needle.

Note, as seen in FIG. 5, proximal segment 120 is affixed to needle hub 80 by a pair of hinges 172 and 174 associated with lateral sides 152 and 154, respectively. Hinges 172 and 174 permit proximal segment 120 to rotate through an angle required to fold and unfold shield 50 about needle 40. Note that as shield 50 folds and unfolds, distal segment 110 rotates about needle 40 in a manner dictated by the interface between yoke 130, needle 40 and arcuate guide surface 140. Note that yoke 130 is free to rotate by hinged attachment through hinges 132 and 134 (see FIGS. 3 and 5) as segment 110 rotates about needle 40. In doing so, yoke 130 remains in alignment with needle 40 and provides a lift and guide as segment so rotates. In this manner, needle tip 100 is untouched by any structure of shield 50. The displacement of needle tip 100 under control of yoke 136 and arcuate guide surface 140 is best seen in combination in FIGS. 4 and 6.

Note in FIG. 5, shield 50 is fully unfolded and extended. Proximal and upward force placed upon button 158 causes shield 50 to unfold through the intermediate state seen in FIGS. 3 and 4 and further to a completely folded state seen in FIG. 2. A distal and arcuately downward force placed upon button 158 causes shield 50 to be displaced from the state seen in FIG. 2 through the state of FIGS. 3 and 4 and further to the unfolded state of FIG. 5. In this manner, needle tip 100 may be alternately protected by shield 50 and removed from shield 50 for use a plurality of times with needle tip 100 being fully protected by an unfolded shield 50 between medical procedures.

Following last use of assembly 30 in a medical procedure, it is preferred that shield 50 be unreleasibly latched as a final precaution. An unreleasible latch or lock may be provided by a number of latching mechanisms within the scope of the instant invention disclosed herein. One such mechanism is seen as a part of assembly 30' in FIG. 7. With the exception of the following disclosed variations, assembly 30' is like assembly 30, earlier described, and, in the same manner, shield 50' is like shield 50. Shield 50' has a top piece 156' which has a button 158, but extending toward a lateral side 152' of a proximal segment 120' (Lateral side 152' is not shown in the figures, but is similar to lateral side 152 of proximal segment 120 of assembly 30 and is therefore referenced by the same number, 152, with a prime.) is a protruding latch part 180. Latch part 180 has the form of an arrow 182 having a pointed end 184 and a pair of juxtaposed ledges 186 and 188.

Juxtaposed pointed end 184 lateral side 152' has a slot 190, partially closed by a pair of ears 192 and 194. Ears 192 and 194 are spaced apart just far enough to permit total entry of arrow or barb 182 into slot 190 by distortion of ledges 186 and 188. Once arrow 182 is so displaced into slot 190 action of ears 192 and 194 against ledges 196 and 188, respectively, unreleasibly retain latch part 180 in slot 190. Note that such an unreleasible latch is accomplished by selectively applying a force upon button 158 which is sufficiently greater than the force to close and affix latch hook 162 of top piece 156' to a transverse bar 146 (see FIG. 6).

Figure 8:
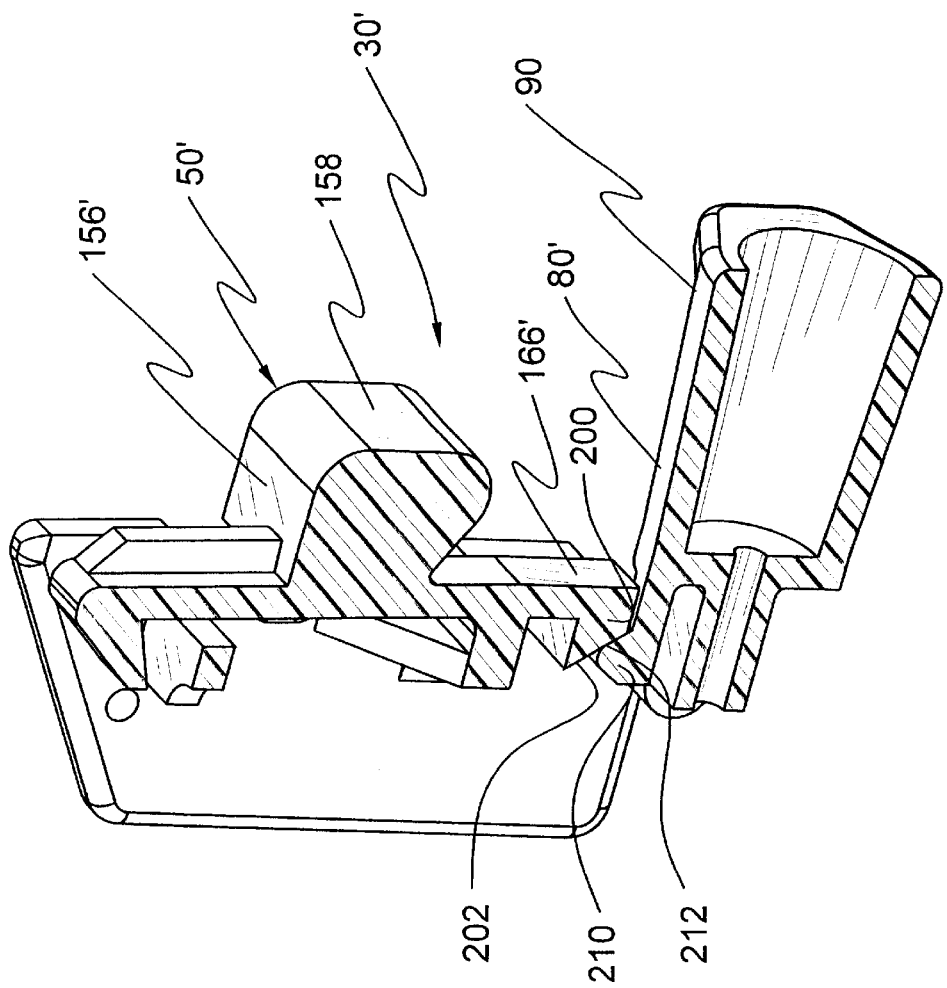
FIG. 8 is a lateral cross section of the assembly seen in FIG. 7 wherein a releasible catch and latch, which constrains the assembly in a stable folded state, is seen.

It is also desirable to assure that shield 50' (and shield 50) is in a stable state when folded. Such assurance is achievable using a releasible latch as well as by friction. One releasible latch is seen in FIG. 8. In FIG. 8, a laterally extending arm 166' of top piece 156' ends in a "j" section 200 having a sloping face which forms a latch 202. To form a catch for latch 202, hub 80' has an outward extending excrescence 210 to form a catch 212. Note, that, when assembly 30' is folded, latch 202 and catch 212 retain shield 50' in a stable, folded state. However, by placing sufficient distally directed force upon button 158, arm 210' is deflected to release latch 202 from catch 212 permitting shield 50' to unfold and protectively cover needle 40 and needle tip 100.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A safety apparatus for reaccessibly shielding a medical needle, said apparatus comprising:
    a hollow bore cannula securely affixed in a hub and having at least one sharpened tip to form the medical needle;
    a part hingedly joined to said hub, said part comprising an elongated shield which comprises a plurality of serially interconnected substantially rigid segments each of which is interconnected to at least one adjacent segment by an intersegment hinge, at least one segment comprising an open orifice, through which said cannula passes to form an axis of intersection about the cannula, and a channel along which the cannula is disposed when the shield is linearly extended, said shield and said hinges being disposed to permit usable access to said sharpened tip in a medical procedure and extending of the shield to a substantially planar disposition along said cannula whereat the cannula is disposed along the channel without said sharpened tip coming in contact with any portion of said shield, said shield further comprising at least one releasable latching member which affixes the shield relative to the cannula, said shield and cannula, in combination, thereby forming a substantially rigid body which protectively encloses and denies access to said sharpened tip unless and until said releasable latching member is selectively actuated to permit refolding said shield and allowing reaccess to said needle and sharpened tip.

2. The safety apparatus according to claim 1 further comprising a selectively actuated unreleasable latch and catch apparatus whereby said shield is unreleasably affixed to said cannula to deny any further access to said needle and sharpened tip.

3. The safety apparatus according to claim 1 wherein a most distal segment of said shield comprises a guide which is disposed about said cannula and which assures that the needle is directed into and out of being sheathed by said shield in such a manner that the needle tip is untouched by any part of the shield.

4. The safety apparatus according to claim 1 wherein a segment which encloses said sharpened tip comprises a closure of its channel distal from the hub.

5. The safety apparatus according to claim 1 wherein said shield and said hub, in combination, comprise a releasable latch and catch mechanism which keeps the shield, when folded, in a stable but selectively releasable state.

6. The safety apparatus according to claim 1 wherein said shield is made as a single, integral molded part.

7. A method for enclosing and reaccessing a sharpened medical needle comprising the steps of:
    (a) providing a safety apparatus for shielding the medical needle, said apparatus comprising a hollow bore cannula securely affixed in a hub and having at least one sharpened tip to form the medical needle and a part hingedly joined to said hub, said part comprising an elongated shield which comprises a plurality of serially interconnected substantially rigid segments each of which is interconnected to at least one adjacent segment by an intersegment hinge, at least one segment comprising an open orifice, through which said cannula passes to form an axis of intersection about the cannula, and a channel along which the cannula is disposed when the shield is linearly extended, said shield and said hinges being disposed to permit usable access to said sharpened tip in a medical procedure and extending of the shield to a substantially planar disposition along said cannula whereat the cannula is disposed along the channel, said shield further comprising at least one releasable latching member which affixes the shield relative to the cannula, said shield and cannula, in combination, thereby forming a substantially rigid body which protectively encloses, without any portion of said shield contacting said sharpened tip, and denies access to said sharpened tip unless and until said releasable latching member is selectively actuated to permit refolding said shield and allowing reaccess to said needle and sharpened tip;
    (b) displacing said shield about said hub and cannula into a compact, folded state such that said needle tip is accessible for a medical procedure;
    (c) at the end of a phase of said medical procedure unfolding and extending the shield about the needle and selectively actuating the releasable latching member; and
    (d) reaccessing the needle by selectively releasing the releasable latching member and refolding the shield to the folded state.

8. The method for enclosing and reaccessing a sharpened medical needle according to claim 7 comprising an additional step (c).

9. The method for enclosing and reaccessing a sharpened medical needle according to claim 8 comprising an additional step (d).

10. The method for enclosing and reaccessing a sharpened medical needle according to claim 7 comprising additional steps of providing an unreleasable latch/catch mechanism.

11. The method for enclosing and reaccessing a sharpened medical needle according to claim 10 comprising an additional step of selectively activating the unreleasable latch/catch mechanism thereby disallowing further use of the needle and needle tip.

* * * * *